(12) United States Patent
Mukkamala

(10) Patent No.: US 7,074,937 B2
(45) Date of Patent: Jul. 11, 2006

(54) METHOD FOR PRODUCTION OF ADDITIVES FOR LUBRICATING OILS

(75) Inventor: Ravindranath Mukkamala, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 318 days.

(21) Appl. No.: 10/663,159

(22) Filed: Sep. 15, 2003

(65) Prior Publication Data

US 2004/0082797 A1    Apr. 29, 2004

Related U.S. Application Data

(60) Provisional application No. 60/420,895, filed on Oct. 24, 2002.

(51) Int. Cl.
*C07D 233/42* (2006.01)
(52) U.S. Cl. .................. 548/300.7; 548/324.1
(58) Field of Classification Search ............. 548/300.7, 548/324.1
See application file for complete search history.

(56) References Cited

U.S. PATENT DOCUMENTS

| | | | |
|---|---|---|---|
| 2,785,175 A | 3/1957 | Christian | |
| 2,806,036 A | 9/1957 | Christian | |
| 2,842,553 A | 9/1958 | Christian | |
| 5,057,612 A | 10/1991 | Worley et al. | |
| 6,602,831 B1 | 8/2003 | Mukkamala | |

FOREIGN PATENT DOCUMENTS

| | | |
|---|---|---|
| DE | 2500313 A | 7/1975 |
| EP | 1227144 A | 7/2002 |
| EP | 1229 023 | 9/2003 |

OTHER PUBLICATIONS

U.S. Appl. No. 10/166,413, filed Jun. 10, 2003, Mukkamala.
Paventi et al., Preparation Of α-Aminothiomides From Aldehydes, *J. Org. Chem.*, vol. 22 pp. 282-289 (1987).
Asinger et al., Zum Substitutionverhalten von Imidazolidin-4-thionen, *Monatshefte Fur Chernie*, vol. 107, pp. 35-41 (1976) Note: Abstract in English, publication in German.
John D. Christian, 4-Imidazolinethiones, *J. Org. Chem.*, vol. 65, pp. 396-399 (1957).

*Primary Examiner*—Laura L. Stockton
(74) *Attorney, Agent, or Firm*—Kenneth Crimaldi

(57) ABSTRACT

A method for making a compound of formula (I)

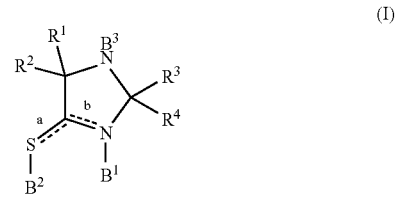

(I)

wherein bonds a and b are single or double bonds, provided that one of a and b is a single bond and the other is a double bond; one of $B^1$ and $B^2$ is —$CHR^5$—$CHR^6$—$C(Y)ZR^7$ and the other is absent; $B^3$ is hydrogen; Y is O or S; Z is O, S or $NR^9$; $R^5$ is hydrogen or $C_1$–$C_4$ alkyl; $R^6$ is hydrogen or $C_1$–$C_4$ alkyl; $R^7$, $R^9$ are independently hydrogen, alkyl, alkenyl, aryl or aralkyl. The method comprises steps of: (a) preparing an imidazolidinethione having formula

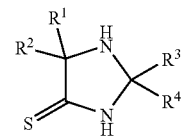

by combining a cyanide source, a sulfide salt, and at least one ketone or aldehyde; and (b) adding to the imidazolidinethione, without isolation of the imidazolidinethione, $CHR^5$=$CR^6$—$C(O)OR^7$.

5 Claims, No Drawings

METHOD FOR PRODUCTION OF ADDITIVES FOR LUBRICATING OILS

CROSS REFERENCE TO RELATED PATENT APPLICATIONS

This is a non-provisional application of prior pending U.S. provisional application Ser. No. 60/420,895 filed Oct. 24, 2002.

BACKGROUND

This invention relates generally to a method for producing oil-soluble additives for lubricating oils.

Zinc dialkyldithiophosphates (ZDDP) are widely used as lubricant additives. The principal disadvantages of these compounds are that an ash residue is produced by the zinc as the additive is consumed, and that phosphorus is known to affect the efficiency of catalytic converters in motor vehicles, thereby causing emissions problems. Imidazolidinethione compounds useful as non-metallic lubricant additives, and processes for their production are disclosed in European Patent Application No. 1,229,023, published Aug. 7, 2002.

The problem addressed by this invention is to find improved processes for producing imidazolidinethione additives, including those disclosed in the aforementioned reference.

STATEMENT OF INVENTION

The present invention is directed to a method for making a compound of formula (I)

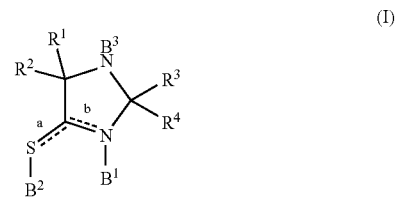
(I)

wherein bonds a and b are single or double bonds, provided that one of a and b is a single bond and the other is a double bond; one of $B^1$ and $B^2$ is —$CHR^5$—$CHR^6$—$C(Y)ZR^7$ or hydrogen and the other is absent; $B^3$ is —$C(W)NHR^8$ or hydrogen; provided that one of $B^1$, $B^2$ and $B^3$ is not hydrogen; $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; provided that at least three of $R^1$, $R^2$, $R^3$ and $R^4$ are alkyl, alkenyl, aryl or aralkyl; Y and W are O or S; Z is O, S or $NR^9$; $R^5$ is hydrogen or $C_1$–$C_4$ alkyl; $R^6$ is hydrogen or $C_1$–$C_4$ alkyl; $R^7$ and $R^9$ are independently hydrogen, alkyl, alkenyl, aryl or aralkyl; and $R^8$ is alkyl, alkenyl, aryl or aralkyl;

said method comprising adding to an imidazolidinethione having formula

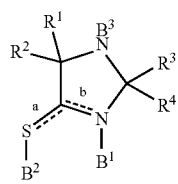

one of: (i) $CHR^5$=$CR^6$—$C(Y)ZR^7$; and (ii) $R^8N$=$C$=$W$ to form a reaction mixture; wherein the reaction mixture is substantially free of solvent.

The present invention is further directed to a method for making a compound of formula (I)

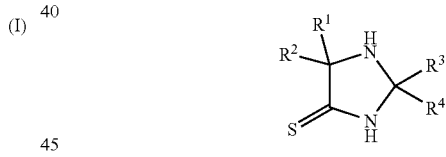
(I)

wherein bonds a and b are single or double bonds, provided that one of a and b is a single bond and the other is a double bond; one of $B^1$ and $B^2$ is —$CR^{10}R^{11}$—$NHR^{12}$ and the other is absent; $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; provided that at least three of $R^1$, $R^2$, $R^3$ and $R^4$ are alkyl, alkenyl, aryl or aralkyl; $R^{10}$ and $R^{11}$ independently are hydrogen, alkyl, alkenyl, aryl or aralkyl; and $R^{12}$ is alkyl, alkenyl, aryl or aralkyl;

said method comprising adding $R^{10}R^{11}C$=O and $R^{12}NH_2$ to an imidazolidinethione having formula

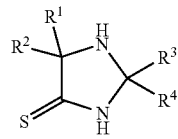

and heating to a temperature from 50° C. to 180° C.

The present invention is further directed to a method for making a compound of formula (I)

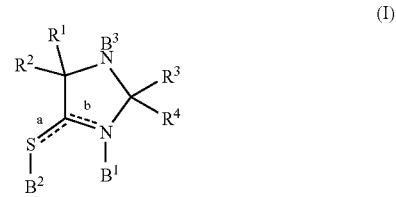
(I)

wherein bonds a and b are single or double bonds, provided that one of a and b is a single bond and the other is a double bond; one of $B^1$ and $B^2$ is —$CHR^5$—$CHR^6$—$C(Y)ZR^7$, —$CR^{10}R^{11}$—$NHR^{12}$ or hydrogen and the other is absent; $B^3$ is —$C(W)NHR^8$ or hydrogen; provided that one of $B^1$, $B^2$ and $B^3$ is not hydrogen; $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; provided that at least three of $R^1$, $R^2$, $R^3$ and $R^4$ are alkyl, alkenyl, aryl or aralkyl; Y and W are O or S; Z is O, S or $NR^9$; $R^5$ is hydrogen or $C_1$–$C_4$ alkyl; $R^6$ is hydrogen or $C_1$–$C_4$ alkyl; $R^7$, $R^9$, $R^{10}$ and $R^{11}$ are independently hydrogen, alkyl, alkenyl, aryl or aralkyl; and $R^8$ and $R^{12}$ independently are alkyl, alkenyl, aryl or aralkyl; said method comprising steps of: (a) preparing an imidazolidinethione having formula

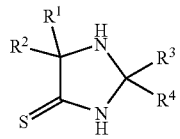

and (b) adding to the imidazolidinethione, without isolation of the imidazolidinethione, one of: (i) $CHR^5=CR^6$—$C(Y)ZR^7$; (ii) $R^{10}R^{11}C=O$ and $R^{12}NH_2$; (iii) $R^{10}R^{11}C=NR^{12}$; and (iv) $R^8N=C=W$.

DETAILED DESCRIPTION

All percentages are weight percentages based on the entire composition described, unless specified otherwise. An "alkyl" group is a saturated hydrocarbyl group having from one to twenty-two carbon atoms in a linear, branched or cyclic arrangement, and having from 0 to 2 oxygen, nitrogen or sulfur atoms. Substitution on alkyl groups of one or more halo, hydroxy, alkoxy, alkanoyl or amido groups is permitted; alkoxy, alkanoyl and amido groups may in turn be substituted by one or more halo substituents. In one preferred embodiment, alkyl groups contain from one to twelve carbon atoms and from 0 to 1 oxygen, nitrogen or sulfur atoms; in another preferred embodiment, alkyl groups contain from 12 to 22 carbon atoms, and more preferably, no heteroatoms. An "alkenyl" group is an "alkyl" group in which at least one single bond has been replaced with a double bond. An "alkanoyl" group is an alkyl group linked through a carbonyl group, e.g., an acetyl group. An "aryl" group is a substituent derived from an aromatic compound, including heterocyclic aromatic compounds having heteroatoms chosen from among nitrogen, oxygen and sulfur. An aryl group has a total of from five to twenty ring atoms, and has one or more rings which are separate or fused. Substitution on aryl groups of one or more halo, alkyl, alkenyl, hydroxy, alkoxy, alkanoyl or amido groups is permitted, with substitution by one or more halo groups being possible on alkyl, alkenyl, alkoxy, alkanoyl or amido groups. An "aralkyl" group is an "alkyl" group substituted by an "aryl" group. A "lubricating oil" is a natural or synthetic oil, or a mixture thereof, having suitable viscosity for use as a lubricant, e.g., as crankcase oil in an internal combustion engine, automatic transmission fluid, turbine lubricant, gear lubricant, compressor lubricant, metal-working lubricant, hydraulic fluid, etc.

Preferably, all of $R^1$, $R^2$, $R^3$ and $R^4$ are alkyl, alkenyl, aryl, aralkyl; or $R^1$ and $R^2$, or $R^3$ and $R^4$, combine with the carbon atom to which they are attached to form an alkyl or alkenyl ring. More preferably all of $R^1$, $R^2$, $R^3$ and $R^4$ are alkyl.

In formula I, the letter a or b represents the total bonding between the atoms adjacent to each letter, e.g., when "a" represents a single bond, the sulfur atom and ring carbon to which it is attached are connected by a single bond. These letters are used in formula I to indicate that the compound may exist in different tautomeric forms, e.g., when the sulfur shown in formula I is substituted, i.e., $B^2$ is present, a is a single bond, b is a double bond and $B^1$ is absent, as will be understood by one skilled in the art.

Preferably, the imidazolidinethione is formed by known methods of combining a cyanide source, a sulfide salt, and at least one ketone or aldehyde. Preferably, the cyanide source is hydrogen cyanide, a water-soluble cyanide salt in combination with an ammonium salt, a ketone cyanohydrin or an aldehyde cyanohydrin. When the cyanide source is hydrogen cyanide, it is combined with ketones or aldehydes, $R^1R^2C=O$ and $R^3R^4C=O$, which may be the same or different. When the cyanide source is a ketone cyanohydrin or an aldehyde cyanohydrin, $R^1R^2C(CN)OH$, it is combined with at least one ketone or aldehyde, $R^3R^4C=O$. When a cyclic ketone is used as a starting material, an imidazolidinethione is produced which has a ring fused to the imidazolidinethione ring at a spiro ring juncture. Preferably, the sulfide salt is an alkali metal or ammonium sulfide, most preferably ammonium sulfide.

Preferably, Y and Z are O, and $R^5$ and $R^6$ independently are hydrogen or methyl. Preferably, $R^7$ is alkyl or aralkyl, more preferably $C_4$–$C_{20}$ alkyl, and most preferably $C_8$–$C_{20}$ alkyl. In one aspect of the invention, a tetraalkylimidazolidinethione (TAIT), or an imidazolidinethione having from one to three alkyl groups, is alkylated with an acrylate ester to produce a compound having a —$CHR^5CHR^6C(O)OR^7$ group, as shown below for an alkyl acrylate, resulting in $R^5=R^6=H$ and $R^7=$alkyl. Reaction with methacrylate or crotonate esters, resulting in $R^5=H$ and $R^6=CH_3$ or $R^6=H$ and $R^5=CH_3$, respectively, also is possible. If $R^1$, $R^2$, $R^3$ and $R^4$ are all methyl, the TAIT is known as TMIT.

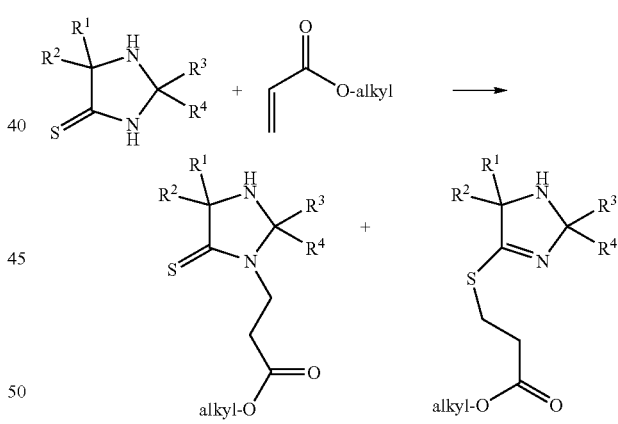

The extent of N-alkylation versus S-alkylation varies with the identity of the R groups on the imidazolidinethione ring and with the alkylating agent, as shown below in the Examples. Preferably, an alkali metal carbonate, most preferably cesium carbonate, is added to promote the reaction. Preferably, the amount of alkali metal carbonate is no more than 10 mole %, based on the amount of acrylate, more preferably no more than 5 mole %.

In another aspect of this invention, a TAIT or an imidazolidinethione having from one to three alkyl groups reacts with an isocyanate or isothiocyanate, $R^8N=C=W$, with W being O or S, respectively, to produce a compound having a —$C(O)NHR^8$ or —$C(S)NHR^8$ group, respectively. Substitution typically occurs on the amine nitrogen of the imidazolidinethione ring. Preferably, $R^8$ is aryl, alkyl or aralkyl, more preferably aryl or $C_8$–$C_{20}$ alkyl. Preferably, W is O. When the isocyanate or isothiocyanate is added to a reaction mixture obtained from preparation of an imidazolidinethione without isolating the imidazolidinethione, preferably substantially all of the water is removed from the reaction mixture by known techniques, i.e., distillation of a water-containing azeotrope, use of drying agents, etc., prior to addition of the isocyanate or isothiocyanate to the reaction mixture.

In one embodiment of the invention, the imidazolidinethione reacts with $CHR^5=CHR^6-C(Y)ZR^7$ or $R^8N=C=W$ substantially in the absence of a solvent. A solvent is any liquid other than the reactants or products of this reaction. Preferably, the reaction mixture contains no more than 5% of solvent by weight, more preferably no more than 2%, more preferably the reaction mixture contains no solvent. Elimination of the solvent increases the efficiency of the process by reducing the cost and the reaction volume. Preferably, the reaction with $CHR^5=CR^6-C(Y)ZR^7$ or $R^8N=C=W$ is performed at a temperature from 50° C. to 180° C., more preferably from 60° C. to 170° C., and most preferably from 90° C. to 130° C. The reaction may be followed by well-known methods to determine reaction completion, e.g., IR spectroscopy. Typically, the reaction is complete in 0.5 to 4 hours. Substitution of acrylate occurs on the thioamide nitrogen or sulfur atom, thereby producing a $-CHR^5-CHR^6-C(Y)ZR^7$ group as $B^1$ or $B^2$, respectively. In contrast, substitution of $R^8N=C=W$ occurs on the amine nitrogen atom of the imidazolidinethione ring, thereby producing a $-C(W)NHR^8$ group as $B^3$.

In another aspect of this invention, a TAIT or an imidazolidinethione having from one to three alkyl groups is alkylated with an imine, $CR^{10}R^{11}=NR^{12}$, or with $R^{10}R^{11}C=O$ and $R^{12}NH_2$, to produce a $-CR^{10}R^{11}-NHR^{12}$ side chain on the thioamide nitrogen or sulfur atom. Use of $R^{10}R^{11}C=O$ and $R^{12}NH_2$ increases the efficiency of the reaction by eliminating the step of pre-forming and isolating the imine from these reagents prior to reaction with the imidazolidinethione. Preferably, $R^{12}$ is $C_{12}$–$C_{22}$ alkyl. Preferably, $R^{10}$ and $R^{11}$ independently are alkyl or hydrogen. In one embodiment of the invention, $CR^{10}R^{11}=NR^{12}$ is a formaldehyde imine, $CH_2=NR^{12}$. In one preferred embodiment, $R^{12}$ is derived from an unsubstituted $C_{16}$–$C_{22}$ alkyl amine, $R^{12}NH_2$, preferably one which is an oil-soluble amine. In one preferred embodiment, the alkyl amine is a tertiary alkyl primary amine, i.e., a primary amine in which the alkyl group is attached to the amino group through a tertiary carbon. Examples of commercially available tertiary alkyl primary amines are the Primene™ amines available from Rohm and Haas Company, Philadelphia, Pa.

Preferably, the imine, $CR^{10}R^{11}=NR^{12}$, or the ketone or aldehyde and amine, $R^{10}R^{11}C=O$ and $R^{12}NH_2$, is heated with the imidazolidinethione to a temperature from 60° C. to 170° C. More preferably, the temperature is from 90° C. to 160° C., and most preferably from 100° C. to 140° C.

In one embodiment of the invention, an imidazolidinethione is prepared, resulting in a reaction mixture containing the imidazolidinethione, a solvent (typically water or a partially aqueous solvent), and possibly starting materials and byproducts. In this embodiment, one of (i) $CHR^5=CR^6-C(Y)ZR^7$; (ii) $R^{10}R^{11}C=O$ and $R^{12}NH_2$; (iii) $R^{10}R^{11}C=NR^{12}$; and (ii) $R^8N=C=W$ is added to the reaction mixture without isolation of the imidazolidinethione. Addition of one of these reagents directly to the imidazolidinethione reaction mixture increases the efficiency of the process by eliminating a costly purification step. In one preferred embodiment, the water is partially or substantially completely removed from the reaction mixture prior to addition of one of the aforementioned reagents.

In one embodiment of the invention, the group $ZR^7$ in a $-CHR^5CHR^6C(Y)ZR^7$ side chain contains a thioethyl group, i.e., a group having the structure $-CH_2CH_2S-$, where one of the $CH_2$ and the sulfur is attached to the $C(Y)$ functionality and the other is attached to an alkyl, alkenyl or aralkyl group. For example, $ZR^7$ can be $OCH_2CH_2S-R$, where R is alkyl, alkenyl or aralkyl; when Y is O, and $R^5$ and $R^6$ are H, the side chain is $-CH_2CH_2C(O)OCH_2CH_2S-R$.

EXAMPLES

Comparative Example 1

Alkylation of Tetraalkylimidazolidinethiones with Alkyl Acrylates

TMIT was prepared according to the procedure given in U.S. Pat. No. 5,057,612, as follows.

To a mechanically-stirred mixture of ammonium sulfide (0.4 moles, 136 mL, 20 wt % aqueous solution), sodium cyanide (14.7 g, 0.3 moles), ammonium chloride (16.1 g, 0.3 moles) and water (80 mL), acetone (44 mL, 0.6 moles) was added drop-wise over a period of 30 min.; during the addition of acetone, the reaction temperature rose to about 36° C. The reaction mixture was then externally heated to 65° C. for a period of 6–7 hours. The reaction mixture was cooled to 0–5° C. using an ice bath, and the white solid was filtered, washed with cold water and suction-dried. The yield of TMIT was 44.6 grams (94%); melting point: 155° C. IR: 3521, 2976, 1657, 1524, 1462 $cm^{-1}$; $^1H$ NMR ($CDCl_3$, 500 MHz): δ 1.46 (s, 6 H), 1.44 (s, 6 H) ppm; $^{13}C$ NMR ($CDCl_3$, 125 MHz): δ 207.7, 78.4, 70.9, 29.9, 29.9 ppm.

Unless otherwise specified, tetraalkylimidazolidinethiones were allowed to react with alkyl acrylates in acetonitrile in the presence of 50 mole % of $Cs_2CO_3$ at room temperature for 10–15 hours (TMIT) to produce compounds having the following structure:

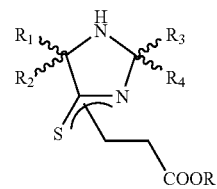

Detailed procedures and product analyses for several products are presented in subsequent Comparative Examples. The acrylates are abbreviated as follows: MA=methyl acrylate; 2-EHA=2-ethylhexyl acrylate; LA=lauryl acrylate; BA=butyl acrylate; and TUA=3-thiaundecyl acrylate. Yield is given in %, the ratio of N-alkylated adduct to S-alkylated adduct (N/S) as a ratio of percentages or as "nd" (not determined), the physical state (state) as "L" (liquid), "SS" (soft solid) or "SG" (sticky gum), and the oil solubility (oil sol) as a weight percent. Oil solubility was measured at room temperature in EXCEL HC 100 lubricating base oil (available from Pennzoil Corp.). The adduct ratio, N/S, was determined from integration of proton NMR signals.

Comparative Example 2

Adduct of TMIT and 2-EHA

A mixture of TMIT (1.0 g, 6.33 mmol), 2-ethylhexyl acrylate (1.16 g, 6.33 mmol) and cesium carbonate (1.0 g, 3.3 mmol) in acetonitrile (15 mL) was stirred at room temperature for 24 h. The reaction mixture was filtered to separate solid cesium carbonate and solvent was evaporated from the filtrate to obtain the product as a colorless oil (1.9 g, 88%). IR: 3325, 2961, 1732, 1595, 1480 cm$^{-1}$; $^1$H NMR (CDCl$_3$, 500 MHz): δ 3.96 (overlapping d, 2 H), 3.83 (t, 1.72 H), 3.22 (t, 0.28 H), 2.82 (t, 1.72 H), 2.71 (t, 0.28 H), 1.91 (bs, 1H), 1.42 (s, 6 H), 1.40 (s, 6H), 1.35–1.20 (m, 8 H), 0.85 (overlapping t, 6 H) ppm; $^{13}$C NMR (CDCl$_3$, 125 MHz): δ 205.8, 173.6, 171.9, 171.3, 130.2, 128.5, 88.7, 82.9, 70.35, 69.6, 67.2, 66.9, 66.8, 40.6, 38.6, 33.9, 31.4, 30.26, 30.21, 28.79, 28.71, 28.23, 25.8, 23.64, 22.83, 13.9, 10.9 ppm. N/S ratio: 86/14.

Comparative Example 3

Adduct of TMIT and LA

A procedure similar to that of Example 2 was used. Starting from TMIT (1.0 g, 6.33 mmol), lauryl acrylate (1.5 g, 6.33 mmol) and cesium carbonate (1.0 g, 3.3 mmol) in acetonitrile (15 mL), the product was isolated as a colorless oil (1.7 g, 68%). IR: 3326, 2925, 1732 1596, 1480 cm$^{-1}$; $^1$H NMR (CDCl$_3$, 500 MHz): δ 4.18 (overlapping d, 2H), 3.86 (t, 1.78 H), 3.36 (t, 0.22 H), 2.85 (t, 1.78 H), 2.75 (t, 0.22 H), 1.90 (bs, 1H), 1.62 (m, 2H), 1.48 (s, 6H), 1.44 (s, 6H), 1.4–1.2 (m, 18H), 0.88 (t, 3H) ppm. N/S ratio: 89/11.

Comparative Example 4

Adduct of TMIT and BA

A procedure similar to that of Example 2 was used. Starting from TMIT (1.0 g, 6.33 mmol), n-butyl acrylate (0.81 g, 6.33 mmol) and cesium carbonate (1.0 g, 3.3 mmol) in acetonitrile (15 mL), the product was isolated as a colorless oil (1.3 g, 72%). IR: 3323, 2961, 1732, 1582, 1483 cm$^{-1}$; $^1$H NMR (CDCl$_3$, 500 MHz): δ 4.08 (t, 2H), 3.85 (t, 2H), 2.84 (t, 2H), 1.95 (bs, 1 H), 1.60 (m, 2H), 1.46 (s, 6H), 1.42 (s, 6H), 1.36 (m, 2H), 0.91 (t, 3H) ppm. N/S ratio: >97/<3.

Comparative Example 5

Adduct of TAIT Mixture Prepared from Acetone/Methyl Isobutyl Ketone/Methyl Ethyl Ketone/Cyclohexanone and EHA A TAIT mixture was prepared from an equimolar mixture of the four title ketones according to the procedure used for preparation of TMIT, using ammonium sulfide (136 mL, 0.4 moles, 20 wt % aqueous solution), sodium cyanide (14.7 g, 0.3 moles), ammonium chloride (16.1 g, 0.3 moles), water (80 mL), cyclohexanone (14.7 g, 0.15 moles), acetone (8.7 g, 0.15 moles) ethyl methyl ketone (10.8 g, 0.15 moles), and methyl isobutyl ketone (15.0 g, 0.15 moles) to obtain an oily layer at the end of the heating period. The oil layer was extracted into chloroform (350 mL), washed with water and dried with anhydrous potassium carbonate. Solvent evaporation yielded the product as a thick oil that slowly turned into a sticky gray solid (36 grams, yield: 55% for an average molecular weight of 220). IR: 3361, 2962, 2874, 1605, 1520, 1459 cm$^{-1}$; $^1$H NMR (CDCl$_3$, 500 MHz): δ 2.24 (d), 2.06 (s), 1.85–1.91 (m), 1.86–1.56 (m), 1.50–1.46 (m), 1.45–1.34 (m), 1.26–1.11 (bm), 1.39 (t), 0.99 (dd), 0.95–0.84 (m) ppm; $^{13}$C NMR (CDCl$_3$, 125 MHz): δ 207.8, 207.62, 207.60, 207.43, 207.40, 207.01, 206.89, 206.68, 206.66, 81.6, 81.18, 81.14, 80.70, 80.65, 78.38, 78.31, 73.95, 73.30, 72.82, 70.79, 70.46, 70.18 and several peaks between 40–10 ppm.

A procedure similar to that of Example 2 was used for the reaction with 2-EHA. Starting from the TAIT product described in the preceding paragraph (1.0 g, ca. 4.5 mmol), 2-ethylhexyl acrylate (0.82 g, 4.5 mmol) and cesium carbonate (0.75 g, 2.25 mmol) in acetonitrile (20 mL), the product was isolated as a yellow oil and solid mixture (1.8 g, 99%). IR: 3325, 2933, 2860, 1732, 1480 cm$^{-1}$.

Comparative Example 6

Adduct of TAIT Mixture Prepared from Methyl Ethyl Ketone and BA

A cis-trans TAIT mixture was obtained by applying the procedure used for preparation of TMIT to ammonium sulfide (136 mL, 0.4 moles, 20 wt % aqueous solution), sodium cyanide (14.7 g, 0.3 moles), ammonium chloride (16.1 g, 0.3 moles), water (80 mL), and ethyl methyl ketone (54.1 g, 0.75 moles) to obtain an oily layer at the end of the heating period. The oil layer was extracted into chloroform (350 mL), washed with water and dried with anhydrous potassium carbonate. Solvent evaporation yielded the product as a thick oil that turned into a sticky dirty-white solid. This solid was washed quickly with cold water and suction dried to give a white powder (23 g, yield: 41%) that melted at 72° C. IR: 3320, 3128, 2966, 1533, 1457, 1371 cm$^{-1}$; $^1$H NMR (CDCl$_3$, 500 MHz): δ 1.85–1.65 (m, 4H), 1.44–1.36 (4s, 6H), 0.99–0.91 (m, 6H) ppm; $^{13}$C NMR (CDCl$_3$, 125 MHz): δ 207.15, 207.07, 81.24, 81.17, 73.69, 73.51, 35.49, 34.99, 33.85, 33.56, 28.56, 28.29, 27.82, 27.24, 8.55, 8.46, 8.25 ppm.

A procedure similar to that of Example 2 was used for the reaction with BA. Starting from the TAIT product described in the preceding paragraph (4.0 g, 21.5 mmol), n-butyl acrylate (2.8 g, 21.5 mmol) and cesium carbonate (3.5 g, 10.8 mmol) in acetonitrile (50 mL), the product was isolated as a yellow oil (6.1 g, 90%). IR: 3351, 2965, 2875, 1732, 1482 cm$^{-1}$; $^1$H NMR (CDCl$_3$, 500 MHz): δ 4.05 (t, 2H), 3.95 (m), 3.80 (m), 3.63 (m), 2.95 (m), 2.82 (m), 2.67 (m), 1.80–1.51 (m, 6H), 1.35 (m, 8H), 0.88 (m, 9H) ppm; $^{13}$C NMR (CDCl$_3$, 125 MHz): δ 205.31, 205.05, 171.2, 85.77, 85.67, 72.44, 72.21, 64.48, 40.28, 34.55, 33.93, 32.65, 33.63, 31.06, 31.03, 30.38, 28.61, 28.21, 26.46, 26.33, 18.91, 13.49 ppm.

Comparative Example 7

Adduct of TMIT and 3-Thiaundecyl Acrylate

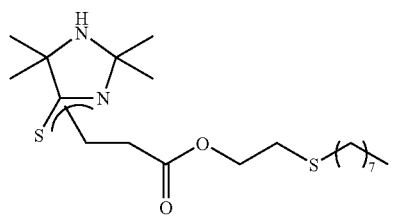

A procedure similar to that of Example 2 was used. Starting from TMIT (1.0 g, 6.33 mmol), 3-thiaundecyl acrylate (1.4 g, 6.33 mmol) and cesium carbonate (1.0 g, 3.3 mmol) in acetonitrile (20 mL), the product was isolated as a light yellow oil (2.0 g, 83%). IR: 2961, 1734, 1481 cm$^{-1}$; $^1$H NMR (CDCl$_3$, 500 MHz): δ 4.22 (t, 2H), 3.84 (t, 2H), 2.84 (t, 2H), 2.71 (t, 2H), 2.52 (t, 2H), 1.55 (m, 2H), 1.46 (s, 6H), 1.42 (s, 6H), 1.4–1.2 (m, 10H), 0.85 (t, 3H) ppm; $^{13}$C NMR (CDCl$_3$, 125 MHz): δ 205.9, 170.9, 82.9, 69.5, 63.7, 40.4, 32.2, 31.6, 31.3, 30.2, 30.1, 29.5, 29.0, 28.6, 28.2, 22.4, 13.9 ppm. N/S ratio: >95/<5.

Comparative Example 8

Adduct of TMIT and an Imine Mixture

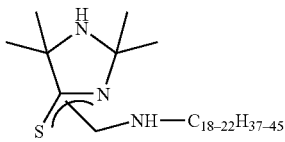

A mixture of TMIT (0.5 g, 3.16 mmol) and the formaldehyde imine (1.17 g, 3.2 mmol) of a mixture of branched C$_{18}$–C$_{22}$ tertiary alkyl primary amines (mixture of amines available from Rohm and Haas Co. under the name Primene™ JM-T Amine) was heated in a sample vial at 120° C. for 1 h and the obtained liquid was cooled to room temperature yielding a thick syrup. IR: 3302, 1672, 1481, 1465, 1377 cm$^{-1}$; $^1$H NMR (CDCl$_3$, 500 MHz): δ 5.4 (bm), 5.1 (s), 4.45–4.33 (5 s), 1.56–0.81 (3 m) ppm; $^{13}$C NMR (CDCl$_3$, 125 MHz): δ 208.4, 208.0, 206.5, 82.78, 82.42, 78.05, 70.88, 69.58, 69.42, 69.27, 68.35, 54.95, and several peaks at 40–14 ppm. The product was soluble in EXCEL HC 100 at 10 weight % at 100° C.; at room temperature, 5% of the solid precipitated overnight.

Comparative Example 9

Adduct of TMIT and an Imine Mixture

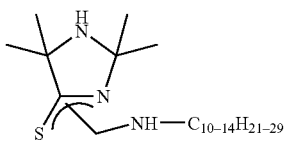

A mixture of TMIT (7.9 g, 50 mmol) and the formaldehyde imine of a mixture of branched C$_{18}$–C$_{22}$ tertiary alkyl primary amines (mixture of amines available from Rohm and Haas Co. under the name Primene™ 81-R Amine) (9.85 g, 50 mmol) were heated in a sample vial at 120–150° C. for about 2 h, and the obtained liquid was cooled to room temperature yielding a thick syrup. IR: 3305, 2959, 1687, 1481, 1465, 1378, 11756, 769 cm$^{-1}$; $^1$H NMR (CDCl$_3$, 500 MHz): δ 4.5–4.3 (bm), 1.5–1.38 (several sharp & overlapping singlets), 1.3–0.7 (bm) ppm; $^{13}$C NMR (CDCl$_3$, 125 MHz): δ 208.6, 208.0, 206.5, 82.79, 82.78, 78.04, 70.88, 69.42, 68.32, 54.42, and several peaks at 35–5 ppm.

Comparative Example 10

Adduct of a Cis-trans Methyl, Ethyl TAIT Mixture and an Imine Mixture

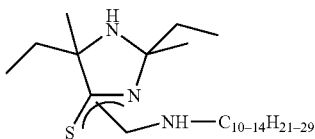

A mixture of cis-trans TAIT mixture prepared from methyl ethyl ketone (see Example 7) (0.56 g, 3 mmol) and the formaldehyde imine of a mixture of branched C$_{18}$–C$_{22}$ tertiary alkyl primary amines (mixture of amines available from Rohm and Haas Co. under the name Primene™ 81-R Amine) (0.59 g, 3 mmol) were heated in a sample vial at 110° C. for 1 h and the obtained liquid was cooled to room temperature yielding a thick syrup. IR: 3311, 3143, 2962, 1689, 1485, 1378, 1161, 787, 738 cm$^{-1}$; $^1$H NMR (CDCl$_3$, 500 MHz): δ 4.95 (m) 4.5–4.0 (m), 2.25 (bm), 1.8–0.6 (three broad multiplets) ppm; $^{13}$C NMR (CDCl$_3$, 125 MHz): δ 207.6, 207.3, 207.2, 206.2, 205.9, 85.6–85.3 (overlapping peaks), 80.9, 80.8, 73.6, 73.4, 72.1, 71.9, 67.9, 54.0, and several peaks at 36–8 ppm.

Example 1

Adduct of TMIT and 2-EHA

A mixture of TMIT (2.37 g, 15 mmol), 2-ethylhexyl acrylate (2.76 g, 15 mmol) and cesium carbonate (0.12 g, 0.38 mmol, 2.5 mole % based on acrylate) was heated in a sand bath at 100–120 ° C. for 2 h, while the progress of the reaction was being followed by IR spectroscopy. The reaction mixture was cooled to room temperature, and to the resulting thick oil was added hexane (40 mL), and the mixture was filtered to remove solid cesium carbonate. Solvent evaporation from the filtrate yielded product as a light-yellow oil (4.4 g, 86%). IR: 3323, 2961, 1733, 1481 cm$^{-1}$.

Example 2

In-situ Generation of Adduct of TMIT and an Imine (from TMIT, a Primene™ Amine and Formaldehyde)

To a mixture of TMIT (1.58 g, 10 mmol) and Primene™ 81-R amine (2.0 g, 10 mmol), formaldehyde (1.2 mL, 37 wt % aqueous solution, 15 mmol) was added at room temperature with stirring. The resulting mixture was heated for 2 h at 65° C., followed by an additional hour of heating between 100–140° C. to complete the reaction as well as remove water and excess formaldehyde from the reaction mixture.

The product was obtained as a yellow syrup (3.13 g, 85%).
IR: 3302, 1672, 1481, 1465, 1377 cm$^{-1}$.

Example 3

Adduct of TMIT and Dodecyl Isocyanate

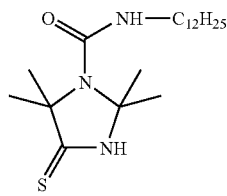

A mixture of TMIT (0.4 g, 0.25 mmol), dodecylisocyanate (0.5 g, 0.25 mmol) was heated in a sand bath at 100–120° C. for 4 h, while the progress of the reaction was being followed by IR spectroscopy. The reaction mixture was cooled to room temperature to obtain a thick oil that slowly solidified into a soft solid (0.9 g, 100%). IR: 3491, 3235, 2924, 2853, 1639, 1515, 1466 cm$^{-1}$; $^1$H NMR (CDCl$_3$, 500 MHz): δ 4.48 (t, 1H), 3.32 (q, 2H), 1.70 (s, 3H), 1.67 (s, 3H), 1.5 (m, 2H), 1.3–1.16 (m, 18H), 0.82 (t, 3H) ppm; $^{13}$C NMR (CDCl$_3$, 125 MHz): δ 207.7, 202.3, 154.2, 80.7, 70.2, 40.5, 31.8, 29.9, 29.5, 29.4, 29.22, 29.19, 28.12, 28.07, 26.9, 22.6, 14 ppm.

What is claimed is:

1. A method for making a compound of formula (I)

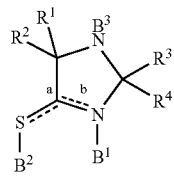

(I)

wherein bonds a and b are single or double bonds, provided that one of a and b is a single bond and the other is a double bond; one of B$^1$ and B$^2$ is —CHR$^5$—CHR$^6$—C(Y)ZR$^7$ and the other is absent; B$^3$ is hydrogen; R$^1$, R$^2$, R$^3$ and R$^4$ are independently hydrogen, alkyl, alkenyl, aryl or aralkyl; or R$^1$ and R$^2$, or R$^3$ and R$^4$, combine with the carbon atom to which they are attached to form an alkyl or alkenyl ring; provided that at least three of R$^1$, R$^2$, R$^3$ and R$^4$ are not hydrogen Y is O or S; Z is O, S or NR$^9$; R$^5$ is hydrogen or C$_1$–C$_4$ alkyl; R$^6$ is hydrogen or C$_1$–C$_4$ alkyl; R$^7$ and R$^9$ are independently hydrogen, alkyl, alkenyl, aryl or aralkyl;

said method comprising adding to an imidazolidinethione having formula

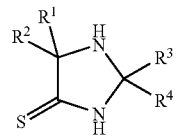

CHR$^5$=CR$^6$—C(Y)ZR$^7$ to form a reaction mixture; wherein the reaction mixture is substantially free of solvent.

2. The method of claim 1 in which CHR$^5$=CR$^6$—C(O)OR$^7$ is added to the imidazolidinethione; R$^5$ is hydrogen; and R$^6$ is hydrogen or methyl.

3. The method of claim 2 further comprising an alkali metal carbonate in an amount less than 10 mole % relative to CHR$^5$=CR$^6$—C(O)OR$^7$.

4. A method for making a compound of formula (I)

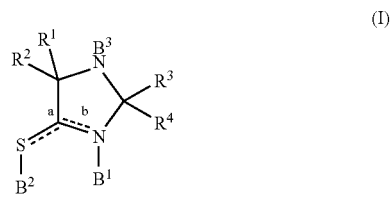

(I)

wherein bonds a and b are single or double bonds, provided that one of a and b is a single bond and the other is a double bond; one of B$^1$ and B$^2$ is —CHR$^5$—CHR$^6$—C(Y)ZR$^7$ and the other is absent; B$^3$ is hydrogen; R$^1$, R$^2$, R$^3$ and R$^4$ are independently hydrogen, alkyl, alkenyl, aryl or aralkyl; or R$^1$ and R$^2$, or R$^3$ and R$^4$, combine with the carbon atom to which they are attached to form an alkyl or alkenyl ring; provided that at least three of R$^1$, R$^2$, R$^3$ and R$^4$ are not hydrogen Y is O or S; Z is O, S or NR$^9$; R$^5$ is hydrogen or C$_1$–C$_4$ alkyl; R$^6$ is hydrogen or C$_1$–C$_4$ alkyl; R$^7$ and R$^9$ are independently hydrogen, alkyl, alkenyl, aryl or aralkyl;

said method comprising steps of:

(a) preparing an imidazolidinethione having formula

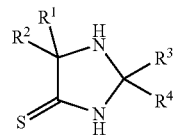

by combining a cyanide source, a sulfide salt, and at least one ketone or aldehyde;

and (b) adding to the imidazolidinethione, without isolation of the imidazolidinethione, CHR$^5$=CR$^6$—C(O)OR$^7$.

5. The method of claim 4 in which CHR$^5$=CR$^6$—C(O)OR$^7$ is added to the imidazolidinethione; R$^5$ is hydrogen; and R$^6$ is hydrogen or methyl.

* * * * *